(12) United States Patent
Kempe et al.

(10) Patent No.: US 9,404,867 B2
(45) Date of Patent: Aug. 2, 2016

(54) LUMINESCENCE MICROSCOPY

(75) Inventors: Michael Kempe, Jena (DE); Ralf Netz, Jena (DE); Gerhard Krampert, Jena (DE)

(73) Assignee: Carl Zeiss Microscopy GmbH, Jena (DE)

( * ) Notice: Subject to any disclaimer, the term of this patent is extended or adjusted under 35 U.S.C. 154(b) by 949 days.

(21) Appl. No.: 13/518,115

(22) PCT Filed: Oct. 22, 2010

(86) PCT No.: PCT/EP2010/065969
§ 371 (c)(1),
(2), (4) Date: Sep. 3, 2012

(87) PCT Pub. No.: WO2011/076458
PCT Pub. Date: Jun. 30, 2011

(65) Prior Publication Data
US 2012/0319007 A1 Dec. 20, 2012

(30) Foreign Application Priority Data
Dec. 22, 2009 (DE) .................. 10 2009 055 216

(51) Int. Cl.
*G01N 21/64* (2006.01)
*G02B 21/16* (2006.01)

(52) U.S. Cl.
CPC ............ *G01N 21/6458* (2013.01); *G02B 21/16* (2013.01)

(58) Field of Classification Search
CPC ................................................ G01N 21/6428
See application file for complete search history.

(56) References Cited

U.S. PATENT DOCUMENTS

| 6,555,826 B2 | 4/2003 | Hoffmann |
| 6,909,105 B1 | 6/2005 | Heintzmann et al. |
| 7,485,875 B2 | 2/2009 | Wolleschensky et al. |

(Continued)

FOREIGN PATENT DOCUMENTS

WO 2009043546 A1 4/2009

OTHER PUBLICATIONS

So et al., "Resolution enhancement in standing-wave total internal reflection microscopy: a point-spread-function engineering approach" vol. 18, No. 11/Nov. 2001/,J. Opt. Soc. Am. A, 13 pages.

(Continued)

*Primary Examiner* — David Porta
*Assistant Examiner* — Hugh H Maupin
(74) *Attorney, Agent, or Firm* — Skaar Ulbrich Macari, P.A.

(57) ABSTRACT

A luminescence microscopy method includes a sample being used, which comprises a certain substance, wherein the certain substance can be converted repeatedly from a first state, in which it can be excited into emitting luminescence radiation, into a second state, in which it cannot be excited into emitting luminescence radiation. The substance present in the sample can be brought into the first state by irradiating switch radiation. The certain substance can be excited into emitting luminescence radiation by irradiating excitation radiation. The sample emitting luminescence radiation can be displayed. A high-resolution selection of sample regions extending perpendicularly to a sample surface is carried out by irradiating either the switch radiation or the excitation radiation as structured illumination of the sample. A high-resolution selection of the sample surface is carried out by irradiating the switch radiation and/or the excitation radiation as TIRF illumination of the sample.

11 Claims, 4 Drawing Sheets

(56) References Cited

U.S. PATENT DOCUMENTS 7,646,481 B2   1/2010   Dyba et al.
2013/0126759 A1*  5/2013   Betzig et al. ............... 250/459.1

OTHER PUBLICATIONS

Hell et al., "Concepts for nanoscale resolution in fluorescence microscopy", Current Opinion in Neurobiology, vol. 14, 2004, pp. 599-609 (11 pages).

Cragg et al., "Lateral resolution enhancement with standing evanescent waves", Optics Letters, vol. 25, No. 1, Jan. 1, 2000, 3 pages.

Thompson et al., "Measuring Surface Dynamics of Biomolecules by Total Internal Reflexion Fluorescence with Photobleaching Recovery or Correlation Spectroscopy", Biophys J., 33, No. 3, Mar. 1981, pp. 435-454 (20 pages).

Hess et al., "Ultra-High Resolution Imaging by Fluorescence Photoactivation localization Microscopy", Biophysical Journal vol. 91(11):4258-4272, Biophysical Society 2006, 15 pages.

International Preliminary Report on Patentability for international application PCT/EP2010/065969, Jul. 10, 2012, 8 pages.

* cited by examiner

LUMINESCENCE MICROSCOPY

PRIORITY

This application claims the benefit of International Application PCT/EP2010/065969filed on Oct. 22, 2010, and German Patent Application No. 102009055216.2, filed on Dec. 22, 2009, both of which are hereby incorporated herein by reference in their entirety.

FIELD

The invention relates to luminescence microscopy and in particular to resolution-enhanced luminescence microscopy.

BACKGROUND

A standard field of use of light microscopy for examining biological preparations is luminescence microscopy. Here, luminescence is understood, as is generally usual, as a generic term for phosphorescence and fluorescence, thus covers both processes. As predominantly fluorescence is used in microscopy, in this description the term fluorescence is often used, but is meant, insofar as technically meaningful, to serve only as an example of processes that generally utilize luminescence.

In luminescence microscopy, particular luminescence dyes (so-called phosphors or fluorophores) are used for the specific tagging of samples, e.g. of cell parts. Samples which luminesce per se, thus without added tagging substance, can also be surveyed. The sample is excited to luminescence with radiation (using so-called excitation radiation) and the excited luminescence light recorded with suitable detectors. For this, a dichroic beam splitter is usually provided in the light microscope in combination with block filters which split the luminescence radiation from the excitation radiation and enable a separate observation. Through this procedure, the representation of individual, differently coloured cell parts in the light microscope is possible. Of course, several parts of a preparation can also be simultaneously coloured with different dyes attaching specifically to different structures of the preparation. This method is called multiple luminescence.

For resolution in standard light microscopy, the wavelength of the radiation used is a determining variable, as according to Ernst Abbe within the framework of an imaging the wavelength used (together with the numerical aperture of the imaging lens system) predetermines the diffraction limit and thus the resolution.

Different approaches have recently been developed for resolutions beyond the diffraction limit. These microscopy methods are characterized by the fact that they provide the user with a higher lateral and/or axial optical resolution compared with the standard microscope. In this description a microscope is described as being of high-resolution if it reaches a resolution beyond the optical diffraction limit. Diffraction-limited microscopes, on the other hand, are called standard microscopes. They realize known optical wide-field microscopy or laser scanning microscopy.

Within the framework of luminescence microscopy, different high-resolution methods attempt to ensure that as far as possible only a volume which is smaller than a minimum volume predetermined by the diffraction limit luminesces. If the degree of volume reduction, e.g. due to the optical parameters of the irradiation, is known, it is known that acquired fluorescence radiation, irrespective of its diffraction-limited broadening during detection, comes from a volume reduced to below the diffraction limit, and a high-resolution image can thus be produced.

This method is used for example in DE 102006009833 A1 which uses so-called reversible saturable optical fluorescence transition (RESOLFT). This microscopy method makes use of a tagging substance which can be repeatedly transformed with the help of a switching beam from a first state in which the tagging substance can be excited to fluorescence into a second state in which no fluorescence can be produced. The named published document describes the state in which the tagging substance can be excited to fluorescence as "fluorescing state A". Naturally, in this first state fluorescence occurs only if the sample is illuminated by excitation radiation, i.e. the sample per se does not fluoresce, but can be excited to do so. In this description, in order to make a clear distinction reference is made to a state that can be excited to fluorescence.

Figure 1:
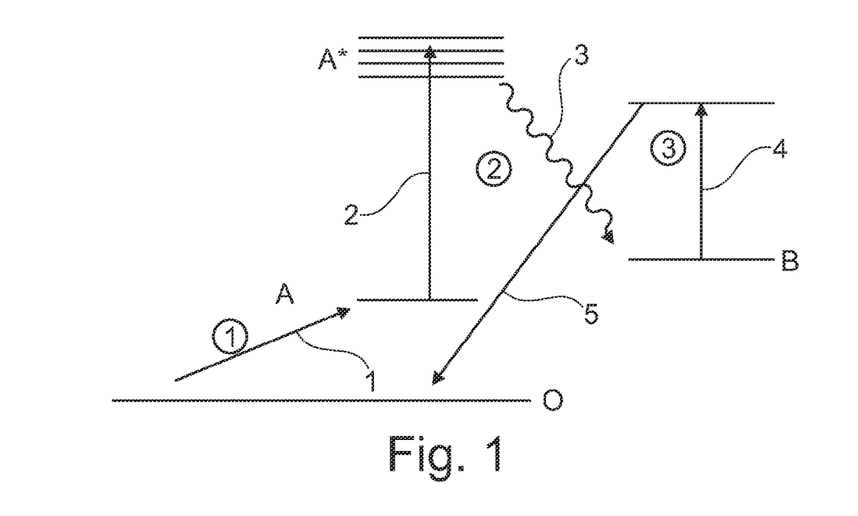

FIG. 1 of the named DE 102006009833 A1 shows in three part-figures a)-c) the three essential part-steps of the microscopy concept described there. The sample is first irradiated with switching radiation, with the result that the sample reaches the state A that can be excited to fluorescence. The illumination is carried out in wide-field (cf. FIG. 1a of the named published document). The sample is then illuminated with a standing-wave field which ensures that only area parts of the sample remain in the fluorescence-capable state A (cf. FIG. 1b of the named published document). Through the standing-wave field which is produced by an interference pattern, this concept means that the sample parts remaining in the fluorescence-capable state A are smaller than the diffraction limit of the optical imaging actually allows. The first two steps thus represent a sample preparation which prepares the sample such that only volume parts of the sample are in a fluorescence-capable state A, wherein, due to the standing-wave field, these parts are in themselves smaller than the diffraction-limited resolution of the optical imaging actually allows. In a last step the thus-prepared sample is then excited to fluorescence. Due to the prior sample preparation, only the parts of the sample which have remained in state A can then emit fluorescence radiation. DE 102006009833 A1 describes the excitation of the prepared sample for the emission of fluorescence radiation as "reading out the fluorescence". For this reading out, i.e. for the excitation of the fluorescence, according to DE 102006009833 A1 the known TIRF concept can also be used in which the fluorescence of the preparation is excited via an evanescent field by irradiating the excitation radiation below the total reflection angle at the boundary between cover glass and sample. This principle known to a person skilled in the art is described for example in the publication by Thompson NL et al., "Measuring Surface Dynamics of Biomolecules by Total Internal Reflexion Fluorescence with Photobleaching Recovery or Correlation Spectroscopy", Biophys J., 33, No. 3, 1981, pp. 435-454.

SUMMARY

The object of the invention is to provide a microscope or a method for luminescence microscopy which allows resolution increased beyond the optical diffraction limit.

This object is achieved according to the invention by a luminescence microscopy method which comprises the following: a sample which contains a specific substance is used, or the sample is provided with this specific substance, wherein the specific substance can be repeatedly transformed from a first state in which it can be excited by light of a specific wavelength to emit luminescence radiation into a second state in which it cannot be excited by light of a specific wavelength to emit luminescence radiation, the specific substance present in the sample is transformed into the first state by irradiation of switching radiation, the specific substance present in the sample is excited to emit luminescence radiation by irradiation of excitation radiation and the sample emitting luminescence radiation is imaged, wherein a high-resolution selection of sample areas extending perpendicular to a sample surface is carried out by irradiating either the switching radiation or the excitation radiation as structured sample illumination, and wherein a high-resolution selection of sample areas extending parallel to the sample surface is carried out by irradiating the switching radiation and/or the excitation radiation as TIRF illumination of the sample.

The object is further achieved by a microscope for luminescence microscopy of a sample which contains a specific substance or is provided with this specific substance, wherein the specific substance can be repeatedly transformed from a first state in which it can be excited to emit luminescence radiation into a second state in which it cannot be excited to emit luminescence radiation, wherein the microscope has: a radiation source and a beam path for irradiating switching radiation onto the sample, in order to transform the specific substance present in the sample into the first state, an excitation radiation source and an excitation beam path for irradiating excitation radiation onto the sample, in order to excite the emission of luminescence radiation in the sample and to transform the specific substance present in the sample into the second state, and a detector and a detection beam path for imaging the sample emitting luminescence radiation, wherein, for high-resolution selection of sample areas extending perpendicular to a sample surface, the switching beam path for irradiating the switching radiation and/or the excitation beam path for irradiating the excitation radiation effect a structured sample illumination, and wherein, for high-resolution selection of sample areas extending parallel to the sample surface, either the switching beam path for irradiating the switching radiation or the excitation beam path for irradiating the excitation radiation effects a TIRF illumination of the sample.

Thus the concept according to the invention switches the sample into a luminescence-capable state in a first switching process. In a second switching process, the sample is excited to luminescence and thereby transformed into a non-luminescence-capable state. In an optional third switching process the sample is returned to the luminescence-capable state. The invention provides that one or both switching processes are a TIRF illumination, and that exactly one of the two switching processes is carried out with a structured illumination, i.e. with a structured wide-field or a structured TIRF illumination. Thus the following options result:

| Variant | Switching process 1 | Switching process 2 |
|---------|---------------------|---------------------|
| 1 | structured TIRF | wide-field |
| 2 | structured TIRF | TIRF |
| 3 | TIRF | structured wide-field |
| 4 | TIRF | structured TIRF |
| 5 | wide-field | structured TIRF |

The invention thus provides a selection of sample areas which extend along the optical axis through a structured illumination which is used either during switching process 1 or during switching process 2. Hence, a separate laborious sample preparation is no longer necessary. Because of that, the microscopy method can be carried out more quickly, which is advantageous in particular when observing biological processes. The corresponding microscope is also simplified, as a separate illumination field for sample preparation need no longer be produced.

The selection perpendicular to the sample surface is usually carried out using a diffraction pattern imaged into the sample. The width of the areas extending perpendicular to the sample surface which are thereby selected is then diffraction-limited. As a result of the mentioned non-linearities, there is a sharpening beyond the diffraction limit. Orthogonally relative to this there is a selection of the sample surface through the irradiation of an evanescent field during switching process 1 and/or during switching process 2. The orthogonal selections through the structured illumination and the evanescent field, which field is called TIRF illumination in this description, selects overall a sample volume which can be smaller both along the optical axis of the imaging of the sample and across it than the diffraction limit allows. In consequence, a high resolution is achieved in two spatial directions.

A further switching process 3 is required if the sample does not automatically return to the fluorescence-capable state after emission of the fluorescence radiation. However, switching processes 1 and 3 can coincide, as is still to be explained. The radiation required for these switching processes is therefore called "switching radiation" here.

The high resolution is improved by the TIRF illumination. This selects the sample surface through the illumination with an evanescent field. The structured illumination increases the resolution through selective excitation perpendicular to the sample surface. The invention uses selection mechanisms which act orthogonally and thereby best complement one another.

The high-resolution microscopy method of the invention can advantageously be combined with the principle known from EP 1157297 B1. Non-linear processes are exploited by means of structured illumination. The saturation of the fluorescence by the structured illumination in switching process 1 or 2 serves as non-linearity. As a result a shift of the object space spectrum takes place relative to the transmission function of the optical system. Specifically, the shift of the spectrum means that object space frequencies $\omega_0$ are transmitted at a spatial frequency $\omega_0 \pm \omega_g$, wherein $\omega_g$ is the frequency of the structured illumination. At a given spatial frequency maximally transmissible by the system, this enables the transfer of spatial frequencies of the object lying above the maximum frequency of the transmission function by the shift frequency $w_g$. This approach requires a reconstruction algorithm for image generation and the utilization of several acquisitions for an image. EP 1157297 B1, also fully incorporated in respect of the corresponding description of the resolving microscopy method, thus uses a structured wide-field illumination of the sample, wherein a stripe modulation is imposed, for example by an amplitude/phase grating. Fluorescence in the sample is also detected in wide-field. The modulation is now brought into at least three different rotation positions, e.g. 0°, 120° and 240°, and the modulation in each rotation position is shifted laterally into at least three different positions. In each shift of the rotation positions (thus in total at least 9 image positions), the sample is detected in wide-field. The grating further has frequencies as close as possible to the limit frequency, which the optical arrangement used is capable of transmitting. The mentioned spectrum shift then takes place using a Fourier analysis, wherein in particular the 0th and +/−1st diffraction order in the images is evaluated. This microscopy principle is also called the SIM (structured illumination microscopy) method.

An improvement of the SIM method can be obtained with a linear illumination which is perpendicular to the stripe direction of the modulation. There is then a linear illumination, wherein the stripe structure recurs along the line. The linear illumination is structured, for its part, by the modulation. The linear illumination allows a confocal slit detection and thus, again, an increase in resolution. This principle is sometimes called SLIM (structured line illumination microscopy).

A further increase in the resolution is obtained when the illumination radiation modulation is carried out on illumination radiation and is so intense that the fluorescence of the sample achieves a saturation into the bright area of the structured illumination. The modulation on the sample then no longer has a sine distribution in respect of the fluorescence, but has still higher harmonics beyond the optical limit frequency because of the saturation effects. This method is also called saturated pattern excitation microscopy (SPEM). In the case of switchable luminescence dyes, as are used for the microscopy according to the invention, this saturation can be achieved with much lower outputs, and reversibly, than with conventional dyes. These three variants of a microscopy which is high-resolution by means of a structured illumination can also be realized as a refinement of the method according to the invention or of the microscope according to the invention.

In this refinement, it is preferred to repeat the irradiation of the switching radiation and the irradiation of the excitation radiation while shifting and/or rotating and/or changing the structure of the structured illumination and to then combine the images obtained during the repetition into a high-resolution image. For this, the microscope provides means for shifting and/or rotating the structure of the structured illumination relative to the sample.

In a particularly easily realized embodiment the fluorescing sample is recorded in a wide-field detection.

It is understood that the features mentioned above and those yet to be explained below can be used, not only in the stated combinations, but also in other combinations or alone, without departing from the scope of the present invention.

BRIEF DESCRIPTION OF THE DRAWINGS

The invention is explained in further detail below by way of example with reference to the attached drawings which also disclose features essential to the invention. There are shown in:

FIG. 1 a term diagram of a substance, or sample constituent, which is suitable for carrying out the invention, FIG. 2 the effect of a sinusoidally modulated illumination field in position and frequency space, FIG. 3 a schematic representation of a microscope for high-resolution luminescence microscopy according to a first embodiment, FIG. 4 a schematic representation of a microscope for high-resolution luminescence microscopy according to a second embodiment and FIG. 5 a schematic representation of a microscope for high-resolution luminescence microscopy according to a third embodiment,

DETAILED DESCRIPTION

FIG. 1 shows the term diagram of a substance which can be provided in a sample or be present there and the luminescence properties, specifically fluorescence properties, of which are used for microscopy. An example of such a substance which is called a dye is the substance DRONPA, which is mentioned and the fluorescence properties of which are described in DE 102005034443 A1 (also with further references there). Starting from a ground state O, the sample is switched by a switching process, in which switching radiation 1 is irradiated, into a state A in which it can be excited to fluorescence. This represents a phase (1). In state A an excited state A* can be achieved by excitation radiation 2. This represents a phase (2).

The sample relaxes from the excited state A*, emitting fluorescence radiation 3, into a state B in which no excitation to fluorescence is possible. By irradiation of reset radiation 4, the sample then returns in a phase (3) via an intermediate status to the ground state O through a reset relaxation 5.

The term structure of FIG. 1 is to be understood merely as an example. The invention is also possible with substances which for example have only the ground states A and B, with the result that phases (1) and (3) are identical. By irradiation of the reset radiation 4 the sample then passes directly from state B to state A from which it can be excited to emit the fluorescence radiation 3. The emission of the fluorescence radiation 3 then returns the sample to state B.

Figure 2:
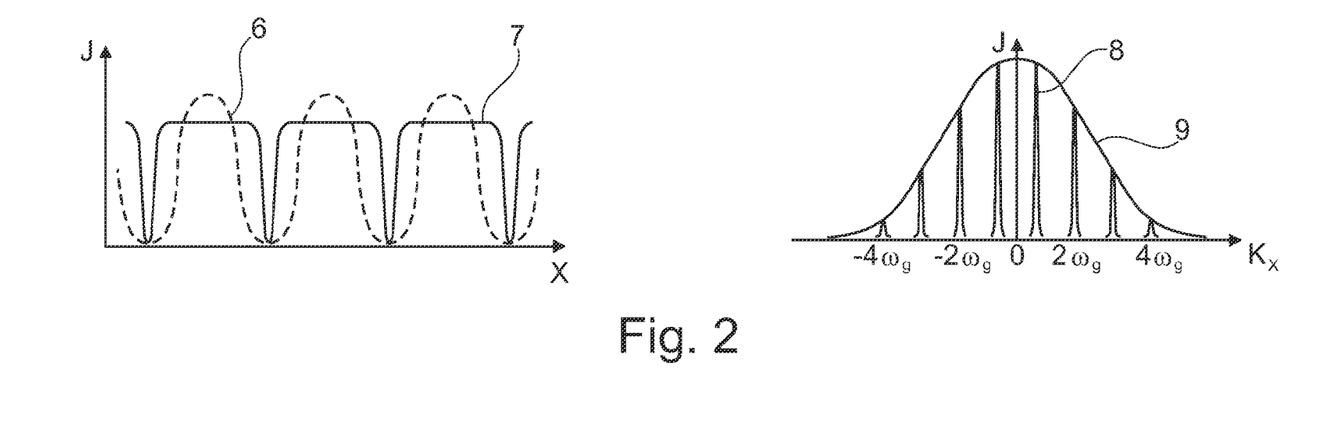

For resolution-enhanced microscopy, either the excitation radiation 2 or the switching radiation 1 (or the reset radiation 4 in systems in which phases (1) and (3) are identical) is carried out with a structured illumination. In the left-hand part-figure of FIG. 2, this is illustrated by a modulated excitation field 6 the intensity of which is plotted by way of example along the x axis. Thus the areas in which no fluorescence is produced when passing from A* to B do not contribute to the acquisition of the fluorescence radiation which occurs e.g. in a wide-field image. The corresponding fluorescence radiation field 7 is plotted in FIG. 2. It can clearly be seen that it has zeros at the zeros of the excitation field 6. Due to a non-linearity, as forms e.g. as a result of saturation of fluorescence by the switching process, the zeros of the fluorescence radiation field 7 are narrower than the zeros of the modulated excitation field 6. If this is produced for example through a difference pattern, zeros are obtained in the fluorescence radiation field 7 which are narrower than the optical resolution actually allows. The steepness of the transition from bright to dark determines which higher-order modulation frequencies are visible in the Fourier transform image which is represented in the right-hand part-image of FIG. 2. By higher-order is meant the second as well as yet higher orders. As the right-hand part-image of FIG. 2 shows, which represents the intensity I in the position-frequency (K) space in one dimension, namely along the $K_x$-axis, the width of the effective optical transfer function 9 (shown schematically here) is increased by the higher modulation frequencies which are given by the nodes 8. The potential optical resolution of the imaging also grows with the width of the transfer function.

Naturally, for this resolution-increasing effect it is not essential to apply the structured field in the form of an excitation field 6. Of course, the structured field can also be used for the radiation which transforms the sample into the state A that can be excited to fluorescence. Depending on the term diagram of the substance used, this can either be the switching radiation 1 or the reset radiation 4. In this description, however, it is assumed for simplicity's sake that the excitation radiation 2 is modulated.

Figure 3:
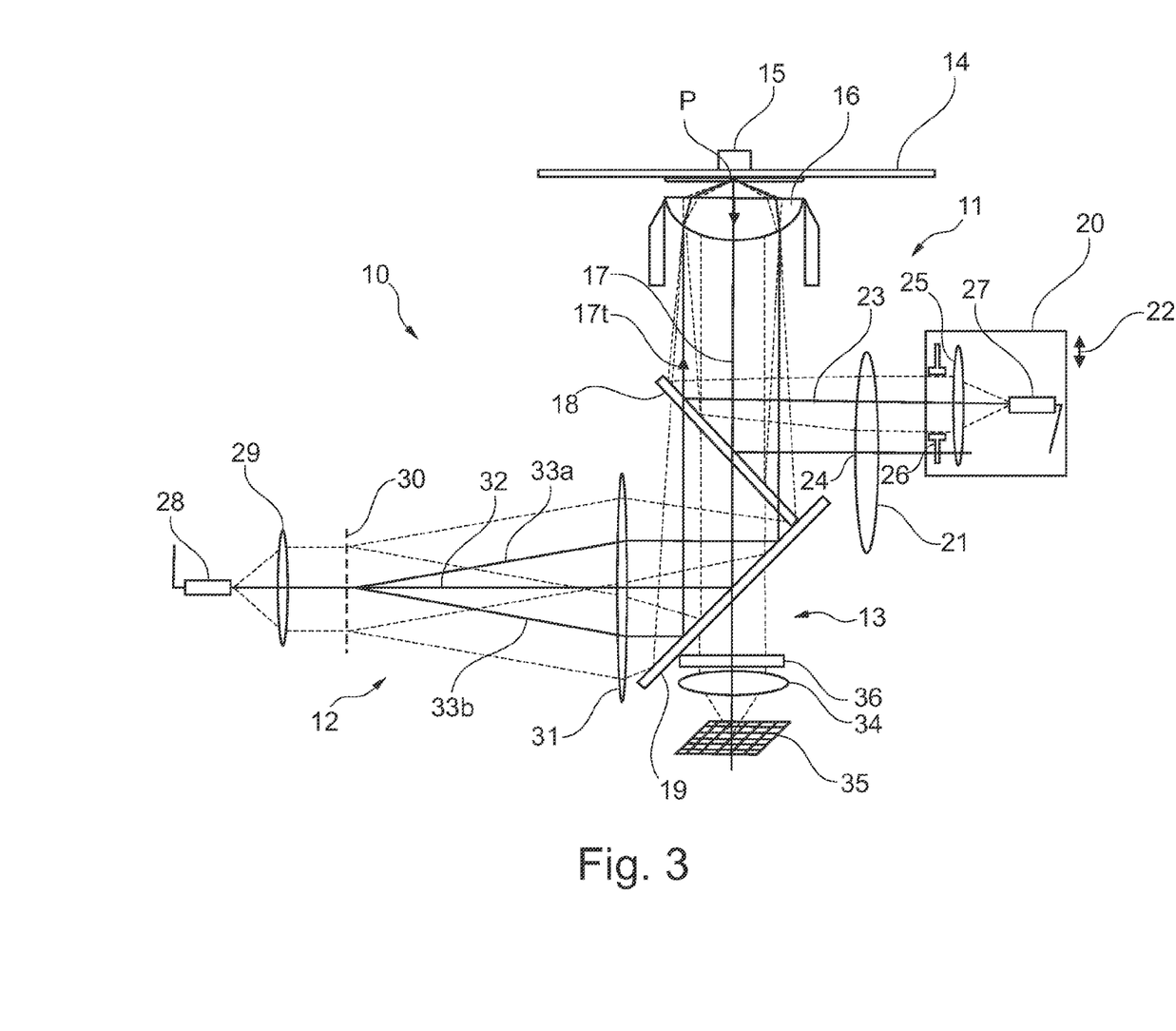

FIG. 3 shows a corresponding microscope 10 in schematic representation. The microscope comprises a switching beam path 11 which effects the switching process (or the reset initiation 4) by irradiation of optical switching radiation as TIRF illumination. The microscope furthermore has an excitation beam path 12 which irradiates the modulated excitation field 6 onto a sample P. This irradiation is also carried out in TIRF illumination. Finally, the microscope also has a detection beam path 13 which records the fluorescence radiation emerging from the sample P in a wide-field detection.

The three beam paths 11, 12, 13 are coupled in onto the sample P via corresponding beam splitters. The sample P is located on a cover glass 14 which lies on a specimen stage 15, with the result that the sample P can be shifted relative to the beam path of the microscope. The sample P is recorded with an objective 16 which has an optical axis 17. Arranged along this optical axis 17 are beam splitters 18 and 19 which reflect the switching beam path 11 (beam splitter 18) or the excitation beam path 12 (beam splitter 19). The switching beam path 11 comprises a switching illumination unit 20 which irradiates the radiation for the switching process 1 (or the reset initiation 4) through a lens system 21. The radiation from the switching beam path 11 is coupled in along an optical axis 17$t$ offset parallel to the optical axis 17 of the objective 16, with the result that the radiation is incident on the sample P at an angle. The angle of incidence is selected via the distance between the optical axis 17$t$ and the optical axis 17 such that a total reflection takes place at the cover glass, as a result of which the sample P is illuminated by an evanescent field, as is known to a person skilled in the art from TIRF microscopy.

To set the distance between the optical axis 17$t$ and the optical axis 17, the switching beam path 11 comprises a shift mechanism 22 which is symbolized in FIG. 3 merely by a double arrow, i.e. in terms of its function. The shift mechanism 22 allows the switching illumination unit 20 to be shifted such that the optical axis 23 along which the radiation from the switching illumination unit 20 emerges travels parallel vis-à-vis the optical axis 24 of the lens system 21. The parallel offset between the optical axes 23 and 24 corresponds, taking into account the inclination of the beam splitter 18, to the parallel offset between the optical axes 17$t$ and 17 and thus sets the angle of incidence of the radiation onto the sample. The shift mechanism 22 thus makes it possible to adjust to the TIRF condition in a simple manner.

The switching illumination unit 20 produces the radiation for the switching process 1 (or for the reset initiation 4) by means of a laser 24 downstream of which are arranged a collimator 25 as well as a diaphragm 26. A parallel ray beam is thus brought about which is then bundled by the lens system 21 onto the objective 16.

The excitation beam path 12 is formed in a similar way. The excitation radiation is provided by a laser 28 which is followed by a collimator 29. Located in the parallel ray beam after the collimator 29 is a pattern generator 30 whose pattern is subsequently imaged into the sample. Thus the pattern generator 30 lies in an intermediate image plane of the imaging. The imaging takes place divergent with respect to the optical axis 32, with the result that the excitation radiation is not incident along the optical axis 17, but on two axes 33$a$, 33$b$ lying laterally displaced thereto. With the help of a subsequent lens system 31, overall a TIRF illumination of the sample P is thus effected which images the pattern of the pattern generator 30 into the sample and excites fluorescence there.

The sample P thus taken to fluorescence is imaged in the detection beam path 13 onto an area detector 35 via a lens system 34. In order to screen out radiation from the switching illumination unit or excitation radiation, a filter 36 which blocks these radiation portions is provided in the detection beam path.

For example a striped pattern is produced in the sample by the pattern generator 30 (e.g. an amplitude and/or phase mask). By applying this pattern to the sample at different angles and in different lateral positions, e.g. by appropriately controlling the specimen stage 15 or by rotating/shifting the pattern in the sample generator 30, a two-dimensional, high-resolution image can be produced using mathematical reconstruction algorithms as they are known for example from EP 1157297 B1 for the SIM method.

Depending on the radiant power required, part of the image field or the whole image field can be illuminated during image acquisition. This can be realized via a zoom system (not shown) in the excitation beam path 12 or in the switching beam path 11.

Figure 4:
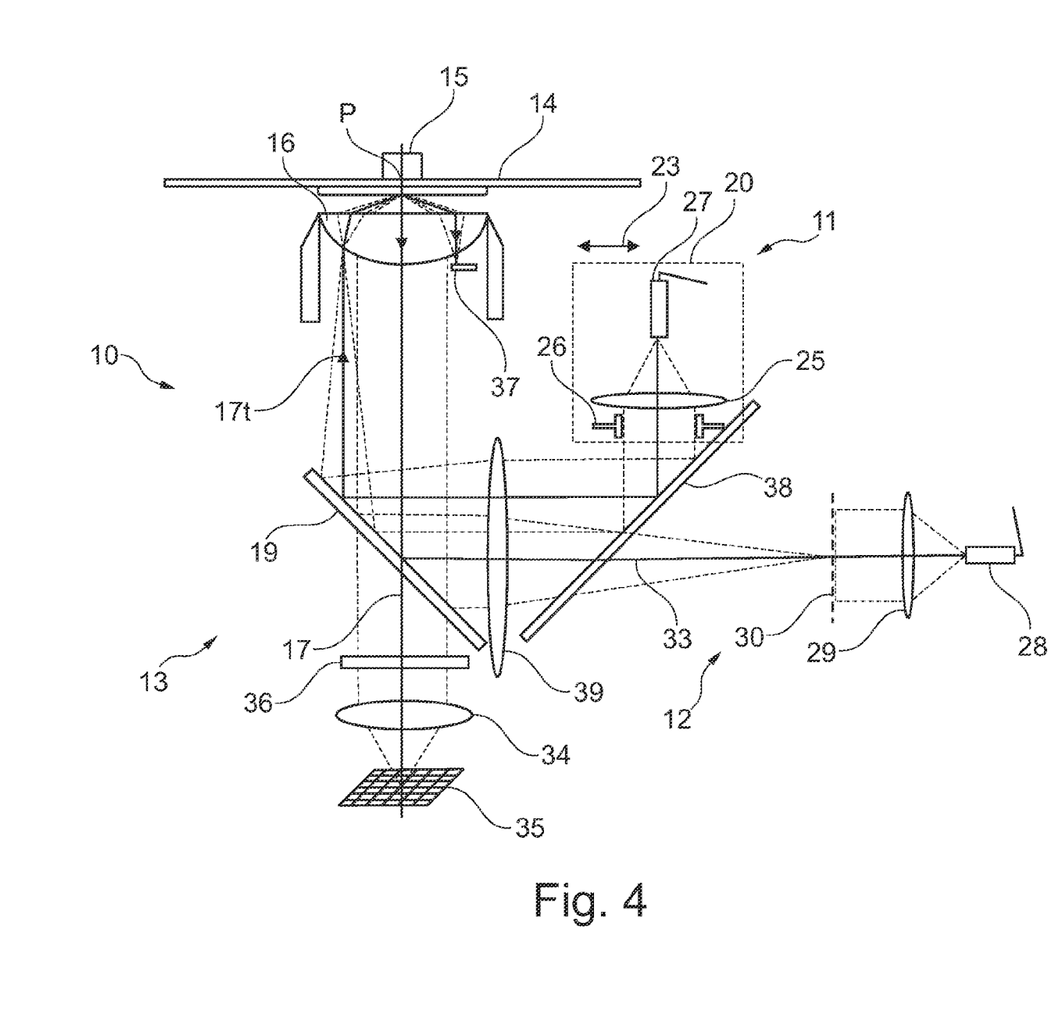

FIG. 4 shows a further design of a microscope 10 many elements of which correspond to those in FIG. 3. In this respect, components in FIG. 4 with a structure or function corresponding to the design in FIG. 3 are given identical references and will not be described again.

In the design in FIG. 4, the switching beam path 11 and the excitation beam path 12 are directed onto the detection beam path 13 via the beam splitter 19. The structured illumination with excitation radiation does not take place in TIRF mode, but as wide-field illumination, i.e. the excitation radiation is incident on an optical axis 33 which is brought into line with the optical axis 17 of the objective 16. The pattern generator 30 stands in the intermediate image of the excitation beam path. On the other hand, the radiation from the switching illumination unit 20 is applied in TIRF illumination which is absorbed following total reflection on a diaphragm 37.

Figure 5:
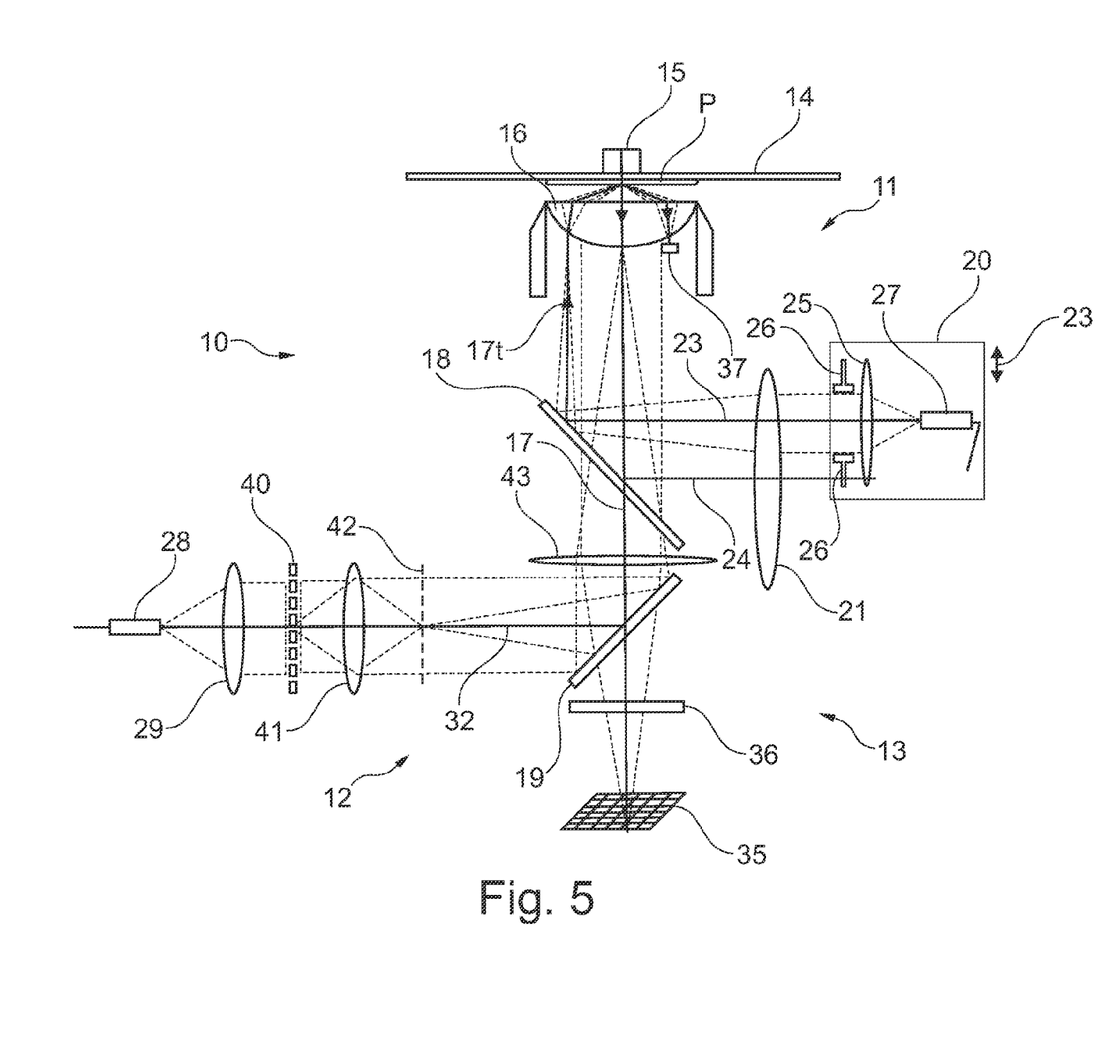

The structured illumination which is used for the RESOLFT process used in the previously described microscopes 10 can also be produced by a suitable amplitude and/or phase mask 40 which stands in a pupil of the objective 16 or a pupil conjugated thereto. This variant is shown in FIG. 5. Here also, elements which correspond to functional or structural elements of previously described designs are given the same references, so that they need not be described again. In the microscope 10 of FIG. 5 the element for structured illumination 40 is imaged into the pupil of the objective 16 via a 4$f$ arrangement, for which a lens system 41 which produces an intermediate image 42 is arranged downstream of the mask 40. The intermediate image 42 is imaged into the sample P, and the image of the fluorescing sample applied to the detector 35, via a lens system 43. As with the design in FIG. 4, the excitation radiation is again incident on the sample P in wide-field illumination.

While the invention has been described in connection with what is presently considered to be the most practical and preferred embodiments, it will be apparent to those of ordinary skill in the art that the invention is not to be limited to the disclosed embodiments. It will be readily apparent to those of ordinary skill in the art that many modifications and equivalent arrangements can be made thereof without departing from the spirit and scope of the present disclosure, such scope to be accorded the broadest interpretation of the appended claims so as to encompass all equivalent structures and products.

The above disclosure is related to the detailed technical contents and inventive features thereof. People skilled in this field may proceed with a variety of modifications and replacements based on the disclosures and suggestions of the invention as described without departing from the characteristics thereof. Nevertheless, although such modifications and replacements are not fully disclosed in the above descriptions, they have substantially been covered in the following claims as appended.

What is claimed is:

1. A luminescence microscopy method comprising:
providing a sample having a sample surface and including a specific substance, wherein the specific substance can be repeatedly transformed from a first state in which it can be excited to emit luminescence radiation into a second state in which it cannot be excited to emit luminescence radiation;
transforming the specific substance present in the sample from the second state into the first state by irradiation of switching radiation; and
exciting the specific substance present in the sample to emit luminescence radiation by irradiation of excitation radiation and imaging the sample emitting luminescence radiation;
wherein one or more sample areas extending perpendicular to the sample surface are selected with high resolution by irradiating one of the switching radiation and the excitation radiation as structured sample illumination being structured in a plane parallel to the sample surface,
and wherein the one or more sample areas extending parallel to the sample surface selected with high resolution by irradiating the other one of the switching radiation and the excitation radiation as TIRF illumination of the sample.

2. The method of claim 1, wherein irradiating the switching beam and irradiating the excitation radiation is repeated while performing at least one of rotating and changing the structure of the structured illumination, and the method further comprising combining the images obtained during the repetitions into a high-resolution image.

3. The method according to claim 2, wherein the specific substance of the sample is transformed by irradiation of reset radiation into a state that cannot be excited to luminescence, and wherein after the imaging the sample is irradiated with reset radiation each time.

4. A microscope for luminescence microscopy of a sample, the sample including a specific substance, wherein the specific substance can be repeatedly transformed from a first state in which it can be excited to emit luminescence radiation into a second state in which it cannot be excited to emit luminescence radiation, the microscope comprising:
a switching radiation source and a switching beam path provided thereto for irradiating switching radiation onto the sample, in order to transform the specific substance present in the sample from the second state into the first state;
an excitation radiation source and an excitation beam path provided thereto for irradiating excitation radiation onto the sample, in order to excite the emission of luminescence radiation in the sample and to transform the specific substance present in the sample into the second state; and
a detector and a detection beam path provided thereto for imaging the sample emitting the luminescence radiation,
wherein, for the high-resolution selection of sample areas extending perpendicular to a sample surface, one of the switching beam path for irradiating the switching radiation and the excitation beam path for irradiating the excitation radiation effects a structured illumination of the sample, wherein this illumination is structured in a plane parallel to the sample surface,
and wherein, for the high-resolution selection of sample areas extending parallel to the sample surface, the other one of the switching beam path for irradiating the switching radiation and the excitation beam path for irradiating the excitation radiation effects a TIRF illumination of the sample.

5. The microscope of claim 4, further comprising a device for rotating the structure of the structured illumination relative to the sample.

6. The microscope of claim 5, further comprising a reset radiation source and a reset radiation path provided thereto for irradiating reset radiation in order to transform the sample into a state that cannot be excited to luminescence.

7. Microscope according to claim 4, further comprising a reset radiation source and a reset radiation path provided thereto for irradiating reset radiation in order to transform the sample into a state that cannot be excited to luminescence.

8. The method of claim 1, wherein irradiating the switching beam and irradiating the excitation radiation is repeated while performing shifting of the structured illumination, the method further comprising combining the images obtained during the repetitions into a high-resolution image.

9. The microscope of claim 4, further comprising a device for shifting the structure of the structured illumination relative to the sample.

10. The method of claim 1, wherein the structured sample illumination is generated by imaging a diffraction pattern into the sample.

11. The microscope of claim 4, wherein the one of switching beam path and excitation beam path images a diffraction pattern into the sample to generate the structured sample illumination.

* * * * *